US006953840B2

(12) United States Patent
Zhu et al.

(10) Patent No.: US 6,953,840 B2
(45) Date of Patent: Oct. 11, 2005

(54) METHODS OF USING NON-HUMAN ANIMAL APOLIPOPROTEIN A-I PROTEIN

(75) Inventors: Lingyu Zhu, Ann Arbor, MI (US); Narendra D. Lalwani, South Lyon, MI (US); Jean-Louis Dasseux, Brighton, MI (US)

(73) Assignee: Esperion Therapeutics, Inc., Ann Arbor, MI (US)

( * ) Notice: Subject to any disclaimer, the term of this patent is extended or adjusted under 35 U.S.C. 154(b) by 0 days.

(21) Appl. No.: 10/629,892

(22) Filed: Jul. 29, 2003

(65) Prior Publication Data

US 2004/0077541 A1 Apr. 22, 2004

Related U.S. Application Data

(60) Provisional application No. 60/399,928, filed on Jul. 30, 2002.

(51) Int. Cl.$^7$ .......................... C07K 1/00; C07K 14/00; C07K 17/00

(52) U.S. Cl. .......................... 530/359; 514/12; 530/350

(58) Field of Search .............................. 514/12, 13, 14, 514/15; 530/324, 326, 327, 328, 359, 350

(56) References Cited

U.S. PATENT DOCUMENTS 6,037,323 A * 3/2000 Dasseux et al. .............. 514/12

OTHER PUBLICATIONS

Schakelford et al., Snthesis and Secretion of Apolipoprotein A1 by chick Breast Muscle, Jun. 10, 1983, The Journal of Biological Chemistry, vol. 258, No. 11, pp. 7175–7180.*
Altschul et al., "Basic Local Alignment Search Tool," 1990, *J Mol Biol* 215(3):403–410.
Altschul et al., "Gapped BLAST and PSI–BLAST: A New Generation of Protein Database Search programs," 1997, *Nucleic Acids Res* 25:3389–3402.
Babin, P.J., et al., "Both Apolipoprotein E and A–1 Genes are Present in a Nonmammalian Vertebrate and are Highly Expressed During Embryonic Development," (1997), *Proc. Natl. Acad. Sci. U.S.A.*, 94(16), pp. 8622–8627.
Banerjee, D., et al., "Biosynthesis of High Density Lipoprotein by Chicken Liver: Intracellular Transport and Proteolytic Processing of Nascent Apolipoprotein A–1," *J Cell Biol.*, (1985), 101(4), pp. 1219–1226.
Beaubatie et al., "Isolation and Characterization of the Major Plasma Apolipoproteins, A–1 and B, in the European Badger, *Meles meles*," 1986, *J Lipid Res* 27:140–149.
Bhattacharyya, N., et al., "Isolation, Characterization and Sequencing of the Chicken Apolipoprotein A1 Encoding Gene," (1991), *Gene*, 104(2), pp. 163–168.
Blaton et al., "Characterization of Babbon Plasma High--Density Lipoproteins and of Their Major Apoproteins," 1977, *Biochemistry* 16:2157–2163.

Brouilette et al., "Structural Models of Human Apolipoprotein A–1: A Critical Analysis and Review," 2001, *Biochim Biophys Acta* 1531:4–46.
Byrnes, L., et al., "Chicken Apolipoprotein A–I:cDNA Sequence, Tissue Expression and Evolution," (1987), *Biochem. Biophys. res. Commun.*, 148(1), pp. 485–492.
Chen and Albers, "Interspecies Activation of Lecithin–Cholesterol Acyltransferase by Apolipoprotein A–I Isolated from the Plasma of Humans, Horses, Sheep, Goats and Rabbits," (1983), *Biochim. Biophys. Acta*, 753(1), pp. 40–46.
Collet, X., et al., "Evolution of Mammalian Apolipoprotein A–I and Conservation of Antigenicity: Correlation with Primary and Secondary Structure," (1997), *J Lipid Res.*, 38(4), pp. 634–644.
Concha, M.I., et al., "Local Expression of Apolipoprotein A–I Gene and a Possible Role for HDL in Primary Defence in the Carp Skin," (2003), *Fish Shellfish Immunol.*, 14(3), pp. 259–273.
Ferrari, S., et al., "The Complete Sequence of Chick Apolipoprotein AI mRNA and Its Expression in the Developing Chick," (1987), *Gene*, 60(1), pp. 39–46.
Frank, P.G., et al., "Apolipoprotein A–I: Structure–Function Relationships," (2000), *J Lipid Res.*, 41(6), pp. 853–872.
GenBank Accession No. NM_000039.
GenBank Accession No. A56858.
GenBank Accession No. JT0672.
GenBank Accession No. A61448.
GenBank Accession No. CAA30377.
GenBank Accession No. X07496.1.
GenBank Accession No. S31394.
GenBank Accession No. LPCHA1.
Goulinet, S., et al., "Plasma Lipoproteins in the Golden Syrian Hamster (*Mesocricetus Auratus*): Heterogeneity of apoB–and apoAI–Containing Particle," (1993), *J Lipid Res.*, 34(6), pp. 943–959.
Gu, Z.W., et al., "Primary Structure of Beijing Duck Apolipoprotein A–1," (1993), *J Protein Chem.*, 12(5), pp. 585–591.
Jackson, R.L., et al., "Isolation and Characterization of the Major Apolipoprotein From Chicken High Density Lipoproteins," (1976), *Biochim. Biophys. Acta.*, 420(2), pp. 342–349.

(Continued)

*Primary Examiner*—Jon Weber
*Assistant Examiner*—Robert Mondesi
(74) *Attorney, Agent, or Firm*—Jones Day

(57) ABSTRACT

The invention provides methods and compositions for treating disorders using non-human animal Apolipoprotein A-I (ApoA-I) protein. The invention provides methods and compositions for treating disorders in animals, including humans, associated with dyslipidemia, including hyperlipidemia, hyperlipoproteinemia, hypertriglyceridemia, hypercholesterolemia, HDL deficiency, ApoA-I deficiency, cardiovascular disease, atherosclerosis, restenosis, and other disorders such as septic shock and viral infections.

33 Claims, No Drawings

OTHER PUBLICATIONS

Januzzi, J.L., et al., "Characterization of the Mouse Apolipoprotein Apoa–1/Apoc–3 Gene Locus: Genomic, mRNA, and Protein Sequences with Comparisons to Other Species," *Genomics*, 14(4), pp. 1081–1088.

Kelley, J.L., et al. "Lipid Transport in the Avian Species. Part I Isolation and Characterization of Apolipoproteins and Major Lipoprotein Density Classes of Male Turkey Serum," (1976), *Atheroscler.*, 24(1–2), pp. 155–175.

Kelley, J.L., et al., "Lipid Transport in the Avian Species. Part 2. Isolation and Characterization of Lipoprotein A and Lipoprotein B, two major Lipoprotein Families of the Male Turkey Serum Lipoprotein System," (1976), *Atheroscler.*, 24(1–2), pp. 177–187.

Kiss, R.S., et al., "Amphipathic Alpha–Helix Bundle Organization of the Lipid–Free chicken Apolipoprotein A–I," (1999), *Biochem.*, 38(14), pp. 4327–4334.

Lamon–Fava, S., et al., "Evolutionary Distinct Mechanisms Regulate Apolipoprotein–A–I Gene expression: Differences Between Avian and Mammalian apoA–I Gene Transcription Control Regions," (1992), *J Lipid Res.*, 33(6), pp. 831–842.

Li, W.H., et al., "The Apolipoprotein Multigene Family: Biosynthesis, Structure, Structure–Function Relationships, and Evolution,", (1988), *J Lipid Res.*, 29(3), pp. 245–271.

Liu, A.C., et al., "Human Apolipoprotein A–I Prevents Atherosclerosis Associated with Apolipoprotein [a] in Transgenic Mice," (1994), *J Lipid Res.*, 35, pp. 2263–2267.

Luo, C.C., et al., "Structure and Expression of Dog Apolipoprotein A–I, E, and C–I mRNAs: Implications for the Evolution and Functional Constraints of Apolipoprotein Structure," (1989), *J Lipid Res.*, 30, pp. 1735–1746.

Mezdour, H., et al., "Exogenous Supply of artificial Lipoproteins does Not Decrease Susceptibility to Atherosclerosis in Cholesterol–fed Rabbits," (1995), *Atheroscler.*, 113, pp. 237–246.

Rajavashisth, T.B., et al., "Structure, Evolution, and Regulation of Chicken Apolipoprotein A–I," (1987), *J Biol. Chem*, 262(15), pp. 7058–7065.

Rubin, E.M., et al., "Inhibition of Early Atherogenesis in Transgenic Mice by Human Apolipoprotein AI," (1991), *Nature*, 353, pp. 265–267.

Segrest, J.P., et al., "Structure and Function of Apolipoprotein A–I and High–Density Lipoprotein," (2000), *Curr. Opin. Lipidol.*, 11(2), pp. 105–115.

Shackleford, J.E., et al., "Synthesis and Secretion of Apolipoprotein A, by Chick Breast Muscle," (1983), *J Biol. Chem.*, 258(11), pp. 7175–7180.

Smith et al., "The Plasma Lipoproteins: Structure and Metabolism," 1978, *Ann Rev Biochem* 47:751–777.

Sparrow et al., "Plasma Lipid Transport in the Preruminant Calf, Bos spp: Primary Structure of Bovine Apolipoprotein A–I," 1992, *Biochim Biophys Acta* 1123:145–150.

Sparrow, D.A., et al., "Plasma Lipid Transport in the Hedgehog: Partial Characterization of Structure and Function of Apolipoprotein A–I," (1995), *J Lipid Res.*, 36(3), pp. 485–495.

Swaney, 1980, *Biochim Biophys Acta* 617:489–502.

Trieu et al., "Sequences and Expression of the Porcine Apolipoprotein A–I and C–III mRNAs," 1993, *Gene* 123(2):173–179.

Trieu et al., "Sequebce of the Porcine ApoA–I Gene," 1993, *Gene* 134 (2):267–270.

Weiler–Guttler, H., et al., "Synthesis of Apolipoprotein A–I in Pig Brain Microvascular Endothelial Cells," (1990), *J Neurochem.*, 54(2), pp. 444–450.

Yang, C.Y., et al., "The Primary Structure of Apolipoprotein A–I from Rabbit High–Density Lipoprotein," (1986), *Eur. J Biochem.*, 160(2), pp. 427–431.

Yang, et al., "The Complete Amino Acid sequence of Proapolipoprotein A–I of Chicken High Density Lipoproteins," (1987), *FEBS Lett.*, 224(2), pp. 261–266.

Yu, F.G., et al., "Characterization of Lipoprotein Secreted by Cultured Eel Hepatocytes and Its Comparison with Serum Lipoproteins," (1991), *Cell Struct Funct.*, 16(4), pp. 347–355.

* cited by examiner

METHODS OF USING NON-HUMAN ANIMAL APOLIPOPROTEIN A-I PROTEIN

This application claims the benefit of U.S. Provisional Application No. 60/399,928, filed Jul. 30, 2002, the entire disclosure of which is incorporated by reference herein in its entirety.

1. INTRODUCTION

The invention provides methods and compositions for treating disorders using non-human animal Apolipoprotein A-I (ApoA-I) protein. The invention provides methods and compositions for treating disorders in animals, including humans, associated with dyslipidemia, including hyperlipidemia, hyperlipoproteinemia, hypertriglyceridemia, hypercholesterolemia, HDL or ApoA-I deficiency, cardiovascular disease, coronary artery disease, atherosclerosis, restenosis, and other disorders such as infections.

2. BACKGROUND OF THE INVENTION

Circulating cholesterol is carried by two major cholesterol carriers, low density lipoproteins (LDL), and high density lipoproteins (HDL). LDL is believed to be responsible for the delivery of cholesterol from the liver (where it is synthesized or obtained from dietary sources) to extrahepatic tissues in the body. It is believed that plasma HDL particles play a major role in cholesterol regulation, acting as scavengers of tissue cholesterol.

Atherosclerosis is a slowly progressive disease characterized by the accumulation of cholesterol within the arterial wall. Compelling evidence indicates that lipids deposited in atherosclerotic lesions are derived primarily from plasma LDL; thus, LDLs have popularly become known as the "bad" cholesterol. In contrast, HDL serum levels correlate inversely with coronary heart disease—indeed, high serum levels of HDL are regarded as a negative risk factor. Each HDL particle contains at least one copy of ApoA-I. It is hypothesized that high levels of plasma HDL are not only protective against coronary artery disease, but can actually induce regression of atherosclerotic plaques (See, Badimon et al., 1992, *Circulation* 86 (Suppl. III):86–94). Thus, HDL has popularly become known as the "good" cholesterol.

A number of treatments are currently available for lowering serum cholesterol and triglycerides (See, Brown & Goldstein, In, The Pharmacological Basis of Therapeutics, 8$^{th}$ Ed., Goodman & Gilman, Pergamon Press, N.Y., 1990, Ch. 36, pp. 874–896). However, each has its own drawbacks and limitations in terms of efficacy, side-effects and qualifying patient population. Antihyperlipidemic agents such as statins (e.g. MEVACOR®, LIPITOR®) can cause life-threatening side effects, such as rhabdomyolysis. In addition, these treatments can be very expensive. The use of human ApoA-I as a treatment has the disadvantages of limited supply and the possibility of disease transmission via blood born pathogens.

There is a need to develop safer and cost effective treatments for lowering serum cholesterol, increasing HDL serum levels, preventing coronary heart diseases and/or treating existing disease, especially atherosclerosis.

3. SUMMARY OF THE INVENTION

The invention provides methods and compositions for treating disorders using non-human animal Apolipoprotein A-I (ApoA-I) protein. The invention provides methods and compositions for treating disorders in animals, including humans, associated with dyslipidemia, including hyperlipidemia, hyperlipoproteinemia, hypertriglyceridemia, hypercholesterolemia, cardiovascular disease, coronary artery disease, atherosclerosis, restenosis, HDL or ApoA-I deficiency and other disorders such as infections, including septic shock and influenza. The method comprises administering to the subject an effective amount of non-human animal ApoA-I protein.

The invention is based, in part, on the Applicants' surprising discovery that non-human animal ApoA-I protein can be used to treat human disorders associated with dyslipidemia and infectious diseases. Such dyslipidemic disorders include hyperlipidemia, hyperlipoproteinemia, hypercholesterolemia, hypertriglyceridemia, cardiovascular disease, coronary artery disease, atherosclerosis, restenosis, HDL deficiency or ApoA-I deficiency. Such infectious disorders include septic shock and viral infections The invention provides methods and compositions for treating diseases in animals, including humans, associated with dyslipidemia, including hyperlipidemia, hyperlipoproteinemia, hypercholesterolemia, hypertriglyceridemia, cardiovascular disease, coronary artery disease, atherosclerosis, restenosis, HDL deficiency and ApoA-I deficiency. The invention also provides methods and compositions for treating diseases in animals, including humans, associated with bacterial or viral infections. The treatment can be therapeutic or prophylactic. Such infections can be, for example, treatment of endotoxemia due to gram negative bacterial infection. The invention also provides methods and compositions for treating viral infections in animals, including humans. Such viral infections include, for example, influenza, human immunodeficiency virus, cytomegalovirus, herpes simplex virus, and the like.

The invention also provides methods for purification of the non-human animal ApoA-I protein, pharmaceutical formulations comprising non-human animal ApoA-I protein, non-human animal ApoA-I protein-lipid complexes and pharmaceutical compositions comprising non-human animal ApoA-I protein-lipid complexes as the active ingredient. The invention further provides methods for preparing such pharmaceutical formulations, methods of administration and other uses of the non-human animal ApoA-I protein.

3.1 DEFINITIONS

The term "dyslipidemia" refers to any altered amount of any or all of the lipids or lipoproteins in the blood. Dyslipidemia can be hyperlipidemia, hyperlipoproteinemia, hypercholesterolemia, hypertriglyceridemia, HDL deficiency, and ApoA-I deficiency. Disorders associated with dyslipidemia include cardiovascular disease, coronary artery disease, atherosclerosis or restenosis. It is to be understood that the term dyslipidemia refers to the disorders, cardiovascular disease, coronary artery disease, atherosclerosis or restenosis. In preferred embodiments, the treatment is for a human disorder.

The term "HDL deficiency" and "ApoA-I deficiency" refers to any decreased amount of HDL or ApoA-I in the blood. The HDL deficiency or ApoA-I deficiency can be a low level or hyponormal level of HDL or ApoA-I. In certain embodiments, the HDL deficiency or ApoA-I deficiency can be an absence of HDL or ApoA-I.

The term "non-human animal ApoA-I" refers to ApolipoproteinA-I obtained from an animal, excluding humans. The non-human animal ApoA-I can be obtained from whole blood of animals, excluding humans, or blood fractions. In certain advantageous embodiments the non-human animal from which the ApoA-I is obtained, can be domesticated and/or commercially raised. In certain embodiments, the non-human animal ApoA-I is obtained from animals slaughtered in large numbers for commercial purposes, such as for meat (e.g. cows, pigs, chickens and turkeys).

The singular forms "a" "an" and "the" include plural reference unless the context clearly dictates otherwise.

The singular form "non-human animal ApoA-I protein" includes the plural reference unless the context clearly dictates otherwise.

4. DETAILED DESCRIPTION OF THE INVENTION

The present invention provides methods and compositions for treating disorders using non-human animal Apolipoprotein A-I (ApoA-I) protein. The invention provides methods and compositions for treating disorders in animals, including humans, associated with dyslipidemia, including hyperlipidemia, hypercholesterolemia, hyperlipoproteinemia, hypertriglyceridemia, cardiovascular disease, coronary artery disease, atherosclerosis, restenosis, HDL deficiency, ApoA-I deficiency and other disorders such as infections including bacterial and viral infections.

The invention is based, in part, on the Applicants' surprising discovery that non-human animal ApoA-I protein can be used to treat disorders associated with dyslipidemia in animals, including humans. Such disorders include hyperlipidemia, hypercholesterolemia, hypertriglyceridemia, hyperlipoproteinemia, cardiovascular disease, coronary artery disease, atherosclerosis, restenosis, HDL deficiency and ApoA-I deficiency. The non-human animal ApoA-I protein can be used to treat animal disorders, including human disorders, associated with infections. In preferred embodiments, the bacterial infection is gram negative bacterial septicemia and the viral infection is influenza.

Advantageously, non-human animal blood can be cheaper, much more abundant and safer than human blood or recombinant source ApoA-I protein. For example, cattle are not known to carry diseases such as human immunodeficiency virus (HIV) and hepatitis which are found in the human blood supply, thus products obtained from bovine blood can be safer for human use than products from human sources. Blood from cattle (bovine), pigs (porcine), chickens and turkeys (avian) is abundantly available either as whole blood or fractions from controlled stocks destined for meat processing, milk and leather production, and other commercial uses. Following collection and purification, the non-human animal ApoA-I protein can be used, alone or as a pharmaceutical formulation (e.g. non-human animal ApoA-I protein/lipid complex) to treat human disorders.

4.1 Methods of Treatment

The non-human animal ApoA-I protein can be used to treat any disorder in animals, especially mammals including humans, for which increasing serum HDL concentration, activating LCAT, and promoting cholesterol efflux and reverse cholesterol transport (RCT) is beneficial. Such conditions include, but are not limited to dyslipidemia, and especially hyperlipidemia, hypercholesterolemia, hypertriglyceridemia, hyperlipoproteinemia, HDL deficiency, ApoA-I deficiency and cardiovascular disease such as coronary artery disease (including, for example, treatment and prevention of angina, myocardial infarction and sudden cardiac death); atherosclerosis (including, for example, treatment and prevention of atherosclerosis); restenosis (including, for example, preventing or treating atherosclerotic plaques which develop as a consequence of medical procedures such as balloon angioplasty); and other disorders, such as infections due to bacteria (including, for example, endotoxemia which can induce septic shock) and viruses (including, for example, influenza A and influenza B).

The non-human animal ApoA-I protein can be used to treat disorders in humans characterized by the accumulation of cholesterol within the arterial wall. The accumulation of cholesterol or plaque within arterial walls is generally a slow progressive disease. The methods of the invention can be used early in the disease process to slow the progression of cholesterol deposits or atherosclerosis, and associated co-morbid disorders. In certain embodiment of the invention, the non-human ApoA-I protein can be used to reverse atherosclerosis.

In certain embodiments, the non-human animal ApoA-I protein can be used to treat cardiovascular disease, for example, those disorders classified by the International Classification of Disease, version 10 codes from 100–199. (U.S. Department of Health and Human Services International Classification of Diseases, $10^{th}$ Revision).

In certain embodiments, the non-human animal ApoA-I protein can treat or prevent disorders associated with dyslipidemia, including hyperlipidemia, HDL deficiency and the like. In certain embodiments, the non-human ApoA-I protein can promote cholesterol efflux, promote reverse cholesterol transport and participate in the delivery of cholesterol esters to the liver.

In certain embodiments, the non-human animal ApoA-I protein can be used to treat infectious disorders, preferably those of bacterial or viral origin. In certain embodiments, the methods can be used to treat sepsis induced by the release of endotoxin that can occur during infection of a subject. While not intending to be bound by any theory, it is believed that the non-human animal ApoA-I protein reduces the release of cytokines that mediate cellular damage during septic shock. In certain embodiments, the non-human animal ApoA-I protein can be used with anti-infective, anti-inflammatory, pressor agents and other drugs or therapies used in the treatment of sepsis, as described below.

In certain embodiments, the methods can be used to treat or prevent viral infections. While not intending to be bound by any theory, it is believed that the α-helices of non-human animal ApoA-I protein bind to a virus, viral particle or viral coat and can prevent infection or facilitate removal of the virus or viral particle from the subject's blood stream or interfere with the viral replication cycle.

The non-human animal ApoA-I protein can be used to treat or prevent any infection in a subject, including a human, caused by a virus. In certain embodiments, the viral infection can be, for example, influenza, rhinovirus, human immunodeficiency virus, hepatitis, cytomegalovirus or herpes simplex virus.

The non-human animal ApoA-I protein can be used alone or in combination with other drugs used to treat the foregoing conditions, as described below. Such therapies include, but are not limited to simultaneous or sequential administration of, for example, other anti-viral drugs.

4.2 Non-Human Animal ApoA-I Protein

In the methods and composition of the present invention the non-human animal ApoA-I protein can be any non-human animal ApoA-I protein know to those of skill in the art.

In certain embodiments, the non-human animal ApoA-I protein is any non-human animal ApoA-I that is useful for treating any disorder in animals, especially mammals, including humans, for which increasing serum HDL concentration, activating LCAT, and promoting cholesterol efflux and reverse cholesterol transport (RCT) is beneficial. In certain embodiments, the non-human animal ApoA-I protein is any non-human animal ApoA-I protein that increases a subjects' HDL concentration, activates LCAT and promotes cholesterol efflux and reverse cholesterol transport. In a preferred embodiment, the subject is human.

Apolipoprotein A-I protein has been identified in a number of non-human animals, for example, cows, horses, sheep, monkeys, baboons, goats, rabbits, dogs, hedgehogs, badgers, mice, rats, cats, guinea pigs, hamsters, duck, chicken, salmon and eel (Brouillette et al., 2001, Biochim. Biophys. Acta 1531:4–46; Yu et al., 1991, Cell Struct. Funct. 16(4):347–55; Chen and Albers 1983, Biochim. Biophys. Acta 753(1): 40–6; Luo et al., 1989, J. Lipid Res. 30(11): 1735–46; Blaton et al., 1977, Biochemistry 16:2157–63; Sparrow et al., 1995, J. Lipid Res. 36(3):485–95; Beaubatie et al., 1986, J. Lipid Res. 27:140–49; Januzzi et al., 1992, Genomics 14(4): 1081–8; Goulinet and Chapman 1993, J. Lipid Res. 34(6): 943–59; Collet et al., 1997, J. Lipid Res. 38(4):634–44; Frank and Marcel 2000, J. Lipid Res. 41(6):853–72).

Apolipoprotein A-I protein derived from non-human animal species are of similar size (Mr≈27,000–28,000) and share considerable homology. (Smith et al., 1978, Ann. Rev. Biochem. 47:751–7). For example, bovine ApoA-I protein comprises 241 amino acid residues and can form a series of repeating amphipathic α-helical regions. There are 10 amphipathic α-helical regions in bovine ApoA-I protein, typically occurring between residues 43–64, 65–86, 87–97, 98–119, 120–141, 142–163, 164–184, 185–206, 207–217 and 218–241 (See, Sparrow et al., 1992, Biochim. Biophys. Acta 1123:145–150 and Swaney 1980, Biochim. Biophys. Acta 617:489–502.) An amino acid sequence comparison between human ApoA-I protein (GenBank Accession Nos. XM_52106 or NM_000039) and bovine ApoA-I protein (GenBank Accession No. A56858) using the program BLAST reveals that the sequences are 77% identical. (Altschul et al., 1990, J. Mol. Biol. 215(3): 403–10).

Pig (porcine) ApoA-I protein comprises about 264 amino acid residues with a molecular weight of about 30,280. GenBank Accession No. S31394, provides a 264 residue porcine ApoA-I sequence with a molecular weight 30,254 while GenBank Accession No. JT0672 provides a 265 residue porcine ApoA-I protein with a molecular weight of 30,320. (See also, Weiler-Guttler et al., 1990, J. Neurochem. 54(2):444–450; Trieu et al., 1993, Gene 123(2): 173–79; Trieu et al., 1993, Gene 134(2): 267–70).

Chicken ApoA-I precursor has 264 amino acid residues; the sequence is provided at GenBank Accession No. LPCHA1. Jackson et al., have described hen ApoA-I as comprising 234 amino acid residues, having a molecular weight of about 28,000 and differing from human ApoA-I by the presence of isoleucine (Jackson et al., 1976, Biochim. Biophys. Acta. 420:(2):342–9). Yang et al., described mature chicken ApoA-I protein as comprised of 240 amino acid residues with a less than 50% homology with humans (See also, Yang et al., 1987, FEBS Lett. 224(2):261–6, see also, Shackelford and Lebherz 1983, J. Biol. Chem. 258(11): 7175–7180, Banjerjee et al., 1985, J. Cell Biol. 101(4): 1219–1226, Rajavashisth et al., 1987, J. Biol. Chem. 262 (15):7058–65, Ferrari et al., 1987, Gene 60(1): 39–46, Bhattacharyya et al., 1991, Gene 104(2):163–168; Lamon-Fava et al., 1992, J. Lipid Res. 33(6):831–42). Circular dichroism studies of chicken ApoA-I protein demonstrate that the protein organizes as a bundle of amphipathic α-helices in a lipid free state (Kiss et al., 1999, Biochemistry 38(14):4327–34). A comparison of secondary structural features among chicken, human, rabbit, dog and rat indicates good conservation of ApoA-I secondary structure with human ApoA-I especially in the N-terminal two-thirds of the protein (Yang et al., 1987, FEBS Lett. 224(2):261–6).

Lipoprotein studies in turkeys have identified an ApoA class of lipoprotein designated in analogy to human ApoA-I and ApoA-II. ApoA-I in turkeys was the major ApoA polypeptide with a molecular weight of about 27,000 (Kelley and Alaupovic 1976, Atherosclerosis 24(1–2): 155–75, Kelley and Alaupovic 1976, Atherosclerosis 24(1–2): 177–87). Duck ApoA-I can comprise about 246 amino acid residues and has a molecular weight of about 28,744 (GenBank Accession No. A61448, Gu et al., 1993, J. Protein Chem. 12(5):585–91).

In certain preferred embodiments, the non-human animal ApoA-I protein is obtained from commercial animals slaughtered during the production of meat or other goods, for example, cows, sheep, pigs, goats, chickens, ducks, turkeys and rabbits. A comparison of the ApoA-I sequences of human, baboon, dog, pig, rabbit, cow, hedgehog, mouse, rat, chicken, duck and salmon indicates that the N-terminal domain of ApoA-I is highly conserved while the central and C-terminal domains show some conservative substitutions among species (Frank and Marcel 2000, J. Lipid Res. 41(6):853–72, Collet et al., 1997, J. Lipid Res. 38(4): 634–44).

Human ApoA-I and ApoA-I agonists form amphipathic α-helices in the presence of lipids. See, U.S. Pat. Nos. 6,004,925; 6,376,464; 6,329,341; 6,046,166 and 6,037,323 and Brouillette et al., 2001, Biochim. Biophys. Acta 1531:4–46, which are incorporated by reference herein. While not intending to be bound by any theory, it is believed that the non-human animal ApoA-I protein has equivalent function and activity in humans as native, human ApoA-I. The helices formed by non-human animal ApoA-I protein are believed to have equivalent function and activity in humans as native, human ApoA-I protein, thereby effecting lipid-binding, cholesterol efflux and LCAT activation. In addition, the amphipathic helices (in the presence of lipids), bind lipids, form pre-β-like or HDL-like complexes, activate lecithin:cholesterol acyltransferase (LCAT), increase serum HDL concentration, including HDL cholesterol and/or HDL protein and promote cholesterol efflux. In fact, any non-human animal ApoA-I protein that can promote cholesterol efflux in humans can be used in the methods of the invention.

In certain embodiments, non-human animal ApoA-I protein is one that has secondary structural features similar to native, human ApoA-I or ApoA-I agonists. In native human ApoA-I, the secondary structure of the protein is predominately α-helices; the monomer comprising about 10 helical regions. (See, Frank and Marcel 2000, J. Lipid Res. 41(6): 852–72 and Brouillette et al., 2001, Biochim. Biophys. Acta 1531:4–46). Helical and hydrophobic properties of the non-human ApoA-I proteins can be conveniently quantitated, such as the hydrophobic moment ($<\mu_H>$), the total hydrophobicity ($<H_0>$), the total hydrophobicity of the hydrophobic face ($H_0^{pho}$) and the hydrophobic angle (pho angle). (See, U.S. Pat. No. 6,004,925, Eisenberg 1984, J. Mol. Biol. 179:125–142, Eisenberg, 1984, Ann. Rev. Biochem. 53:595–623, Eisenberg et al., 1982, Nature 299: 371–374).

In certain embodiments, the helical and hydrophobic properties, described below, pertain to a monomeric non-human animal ApoA-I protein. In certain embodiments, the helical and hydrophobic properties pertain to a single helix in a non-human animal ApoA-I protein. In certain embodiments, the non-human animal ApoA-I protein has a hydrophobic moment, ($<\mu_H>$), in the range of about 0.45 to about 0.65, preferably between about 0.50 to about 0.60. In certain embodiments, the non-human animal ApoA-I protein has a total hydrophobicity, ($<H_0>$), in the range of about −0.030 to about −0.070. In certain embodiments, the non-human animal ApoA-I protein has a total hydrophobicity of the hydrophobic face, ($H_0^{pho}$), in the range of about 0.90 to about 1.2, preferably from about 0.94 to about 1.1. In certain embodiments, the non-human animal ApoA-I protein has a hydrophobic angle (pho angle) in the range of about 160° to about 220° preferably from about 180° to about 200°.

In certain embodiments, the non-human animal ApoA-I comprises amphipathic α-helices. In another embodiment, the non-human animal ApoA-I activates LCAT and promotes cholesterol efflux. Methods for determining LCAT activation have been described, for example, in U.S. Pat. Nos. 6,004,925, 6,046,166 and 6,037,323. See also, Chen and Albers for an multispecies comparison and intraspecies LCAT activation activity (1983, Biochim. Biophys. Acta 753(1):40–6). In certain embodiments, the non-human animal ApoA-I protein has greater than about 38% human LCAT activation activity. In certain embodiments, the non-human animal ApoA-I protein has greater than about 40%, greater than about 43% or greater than about 45% human LCAT activation activity.

In certain embodiments, the non-human animal ApoA-I protein has some homology with native, human ApoA-I. The term homology, refers to the non-human animal ApoA-I protein having greater than about 60%, greater than about 70%, preferably greater than about 80% or most preferably greater than about 90% amino acid residue sequence identity with native human ApoA-I or a BLAST score (Altschul et al., 1997, Nucleic Acids Res. 25:3389–402) of 1×10–6 over at least 100 amino acids with native human ApoA-I (GenBank Accession No. CAA30377) or the sequence encoded by the nucleotide sequence described in Genbank Accession No. X07496.1.

It is generally accepted that lipopolysaccharide is the causative substance of the sequelae of gram negative septicemia (Casas et al., 1995, J. Surgical Res. 59:544–552). The effects of lipopolysaccharide do not appear to be direct but rather the lipopolysaccharide appears to activate the release of cytokines which in turn leads to cellular damage and organ dysfunction. One prominent cytokine responsible for septic shock is tumor necrosis factor-α (TNF-α). Casas et al. have described the reduction of TNF-α production in in vitro, ex-vivo and in-vitro model systems (1995, J. Surgical Res. 59:544–552, incorporated herein by reference in its entirety).

The non-human animal ApoA-I protein can be any non-human animal ApoA-I protein that decreases the morbidity of septicemia, including improving or alleviating accompanying disorders, such as hypotension, acidosis, tissue damage and multiple organ system failure. In certain embodiments, the non-human animal ApoA-I protein reduces the release of cytokines, including tumor necrosis factor-α production. TNF-α reduction can be measured, in vivo (TNF-α production upon lipopolysaccharide challenge in whole blood), ex vivo or in vitro (by comparison of TNF-α levels following lipopolysaccharide challenge in rabbits) as described below and by Casas et al., 1995, J. Surgical Res. 59:544–552.

In certain embodiments, the non-human animal ApoA-I protein exhibits about greater than 50% reduction in TNF-α production upon lipopolysaccharide challenge versus a control in either an in vitro, whole blood assay, or in an ex vivo or in vitro lipopolysaccharide challenge in a rabbit, as described below. In certain embodiments, the non-human animal ApoA-I protein exhibits about greater than 55% reduction in TNF-α production, preferably about greater than 60%, preferably about greater than 65% and most preferably about 70% or greater reduction in TNF-α production in vitro.

The non-human animal ApoA-I protein can be administered as a pharmaceutical formulation either alone or complexed with a lipid, for example, sphingomyelin. The non-human animal ApoA-I protein can be given by any route of administration and in any dose. It will be apparent to one of skill in the art that the route of administration, dose and frequency of administration will depend on factors such as pharmacokinetics, pharmacodynamics and patient specific factors including, for example, the severity of illness.

The non-human animal ApoA-I protein can be used in combination with any one or more cholesterol lowering therapies; e.g., bile-acid resins, niacin, fibrates and/or statins, or combinations thereof, for the treatment of hypercholesterolemia or atherosclerosis. Such a combined regimen may produce particularly beneficial therapeutic effects since each drug acts on a different target in cholesterol synthesis and transport; i.e., bile acid resins affect cholesterol recycling, the chylomicron and LDL population; niacin primarily affects the VLDL and LDL population; the statins inhibit cholesterol synthesis, decreasing the LDL population (and perhaps increasing LDL receptor expression); whereas the non-human animal ApoA-I protein affects RCT, increases HDL, increases LCAT activity and promotes cholesterol efflux.

For example, the non-human animal ApoA-I protein or protein-lipid complex can be used with any dyslipidemia drug, e.g. cholestyramine (QUESTRAN®), colestipol (COLESTID®), colesevelam (WELCHOL®), lovastatin (MEVACOR®), simvastatin (ZOCOR®), pravastatin (PRAVACHOL®), fluvastatin (LESCOL®), atorvastatin (LIPITOR®), rosuvastatin (CRESTOR®), pitavastatin (NK-104), pravastatin/aspirin (PRAVIGARD®), niacin/lovastatin (NICOSTATIN®), clofibrate (ATROMID-S®), gemfibrozil (LOPID®), fenofibrate (TRICOR®), niacin (NIASPAN®) and ApoA-I agonists and ApoA-I agonist/lipid complexes (U.S. Pat. Nos. 6,004,925, 6,376,474, 6,046,166, 6,037,323 and 6,265,377, incorporated herein by reference in its entirety).

The non-human animal ApoA-I protein or protein-lipid complex can be used in combination with anti-microbial drugs, anti-inflammatory drugs and other drugs used to treat septic shock induced by endotoxin, e.g. drugs to treat sepsis can be, drotrecogin (XIGRIS®), PAFASE® (ICOS), E-5531 (Eisai), VX-799 (Vertex), SEGARD® (Knoll) and ApoA-I agonists and ApoA-I agonist/lipid complexes (U.S. Pat. No. 6,329,341, incorporated herein by reference in its entirety).

The non-human animal ApoA-I protein can be used alone or in combination to treat any disorder in animals, especially mammals including humans, associated with viral infections. Such infecting viruses include, but are not limited to influenza, rhinovirus, herpes simplex, cytomegalovirus, human immunodeficiency virus and Ebola. Influenza infections include those that develop as a result of infection with, for example, influenza A, influenza B or influenza C virus. The non-human animal ApoA-I protein can be used for the therapeutic or prophylactic treatment of subjects known or suspected of being infected by a virus or at risk of becoming infected from the viruses described above. The non-human animal ApoA-I protein can be used to treat or prevent human influenza caused by influenza A, B or C virus.

The non-human animal ApoA-I protein can be used in combination with other drugs used to treat infections. For example, the non-human animal ApoA-I protein can be used with vaccines and any anti-infection drugs e.g., foscarnet (FOSCAVIR®), ganciclovir (CYTOVENE®), valganciclovir (VALCYTE®), acyclovir (ZOVIRAX®), famciclovir (FAMVIR®), valcyclovir (VALTREX®), amantadine (SYMMETREL®), cidofovir (VISTIDE®), ribavirin (REBETOL®), rimantadine (FLUMADINE®), zanamivir (RELENZA®), oseltamivir (TAMIFLU®), saquinavir (INVIRASE®), ritonavir (NORVIR®), indinavir (CRIXIVAN®), nelfinavir (VIRACEPT®), amprenavir (AGENERASE®), lopinavir/ritonavir (KALETRA®), tenofovir disoproxil (VIREAD®), didanosine (VIDEX®), lamivudine (EPIVIR®), stavudine (ZERIT®), zalcitabine (HIVID®), zidovudine (RETROVIR®), abacavir (ZIAGEN®), abacavir/lamivudine/zidovudine (TRIZIVIR®), lamivudine/zidovudine (COMBIVIR®), nevirapine (VIRAMUNE®), delavirdine (RESCRIPTOR®) and efavirenz (SUSTEVA®).

4.3 Purification

For use in the methods and composition of the present invention, the non-human animal ApoA-I protein can be purified by any means known to those of skill in the art.

For instance, the non-human animal ApoA-I protein can be purified from non-human animal blood collected by any means. Advantageously, the blood can be from controlled animals destined for commercial processing. The blood can be whole blood or fraction thereof.

The non-human animal ApoA-I protein can be purified by techniques such as precipitation through solvent or desalting, reverse phase chromatography, high performance liquid chromatography, ion exchange chromatography, gel electrophoresis, affinity chromatography and the like. The actual conditions used to purify non-human animal ApoA-I protein will depend, in part, on factors such as net charge, hydrophobicity, hydrophilicity, and the like, and will be apparent to those having skill in the art.

Solvent or desalting techniques known in the art can be used to purify the non-human animal ApoA-I protein. For example, the non-human animal ApoA-I protein can be purified by the use of urea, chloroform and ethanol in appropriate concentrations as described in Peitsch, et al., 1989, *Analytical Biochem.* 178: 301–5. The non-human animal ApoA-I protein can also be purified by suspension of plasma fractions in buffer solutions as described in U.S. Pat. No. 5,089,602. An aqueous two-phase extraction followed by temperature-induced phase separation can also be used as described in Persson et al., 1998, *J. Chromatogr.* 711: 97–109.

For affinity chromatography purification, any antibody which specifically binds the non-human animal ApoA-I protein can be used. For the production of antibodies, various host animals, including, but not limited to, rabbits, mice, rats, etc., can be immunized by injection with a protein. The non-human animal ApoA-I protein can be attached to a suitable carrier, such as BSA, by means of a side chain functional group or linkers attached to a side chain functional group. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, proteins, oil emulsions, keyhole limpet hemocyanin, dinitrophenol, and potentially useful human adjuvants such as BCG (bacilli Calmette-Guerin) and *Corynebacterium parvum*.

Monoclonal antibodies to the non-human animal ApoA-I protein can be prepared using any technique which provides for the production of antibody molecules by continuous cell lines in culture. These include but are not limited to the hybridoma technique originally described by Kohler and Milstein, 1975, *Nature* 256:495–497, or U.S. Pat. No. 4,376,110 which is incorporated by reference herein; the human B-cell hybridoma technique; Kosbor et al., 1983, *Immunology Today* 4:72; Cote et al., 1983, *Proc. Natl. Acad. Sci. U.S.A.* 80:2026–2030); and the EBV-hybridoma technique (Cole et al., 1985, *Monoclonal Antibodies and Cancer Therapy*, Alan R. Liss, Inc., pp. 77–96 (1985)). In addition, techniques developed for the production of "chimeric antibodies" (Morrison et al., 1984, *Proc. Natl. Acad. Sci. U.S.A.* 81:6851–6855; Neuberger et al., 1984, *Nature* 312:604–608; Takeda et al., 1985, *Nature* 314:452–454, U.S. Pat. No. 4,816,397; U.S. Pat. No. 4,816,567; which are incorporated by reference herein) by splicing the genes from a mouse antibody molecule of appropriate antigen specificity together with genes from a human antibody molecule of appropriate biological activity can be used. Or "humanized" antibodies can be prepared (see, e.g., Queen, U.S. Pat. No. 5,585,089 which is incorporated by reference herein). Alternatively, techniques described for the production of single chain antibodies (U.S. Pat. No. 4,946,778) can be adapted to produce protein-specific single chain antibodies.

Antibody fragments which contain deletions of specific binding sites can be generated by known techniques. For example, such fragments include but are not limited to F(ab')$_2$ fragments, which can be produced by pepsin digestion of the antibody molecule and Fab fragments, which can be generated by reducing the disulfide bridges of the F(ab')$_2$ fragments. Alternatively, Fab expression libraries can be constructed (Huse et al., 1989, *Science* 246:1275–1281) to allow rapid and easy identification of monoclonal Fab fragments with the desired specificity for the protein of interest.

The antibody or antibody fragment specific for the non-human animal ApoA-I protein can be attached, for example, to agarose, and the antibody-agarose complex is used in immunochromatography to purify proteins. See, Scopes, 1984, *Protein Purification: Principles and Practice*, Springer-Verlag New York, Inc., NY, Livingstone, 1974, Methods In Enzymology: Immunoaffinity Chromatography of Proteins 34:723–731.

The non-human animal ApoA-I protein can be purified using any chromatographic method known to one of skill in the art. For example, the non-human animal ApoA-I protein can be purified by anion-exchange chromatography. See, Mezdour, et al., 1987, *J. Chromatogr.* 20: 35–45, Weisweiler, 1987, *Clin. Chim. Acta.* 169: 249–54 and Ross, et al., 1985, *Anal. Biochem.*149: 166–68 which are incorporated by reference herein. The non-human animal ApoA-I protein can be purified using anion-exchange chromatography, typically used for eliminating endotoxins from proteins such as urokinase, interferon, asparaginase and albumin. See, Sharma 1986, *Biotech. Applied Biochem* 8: 5–22. Removal of endotoxin from apolipoproteins can present an obstacle, however, chromatographic methods for removing endotoxin from apolipoprotein A and apolipoprotein E have been described. See, U.S. Pat. Nos. 5,834,596 and 6,107,467 which are incorporated by reference herein.

There are other purification methods that can be used for purification of non-human animal ApoA-I protein, such as the methods described in U.S. Pat. No. 5,525,472.

4.4 Pharmaceutical Compositions

For use in the methods and compositions of the present invention, the non-human animal ApoA-I protein can be any pharmaceutical composition known to those of skill in the art.

For example, the pharmaceutical composition can contain non-human animal ApoA-I protein or non-human animal ApoA-I protein-lipid complex ("protein-lipid complex") as the active ingredient in a pharmaceutically acceptable carrier suitable for administration and delivery in vivo. Because the non-human animal ApoA-I protein can contain acidic and/or basic termini and/or side chains, the non-human animal ApoA-I protein can be included in the compositions in either the form of free acids or bases, or in the form of pharmaceutically acceptable salts.

Injectable compositions include sterile suspensions, solutions or emulsions of the active ingredient in aqueous or oily vehicles. The compositions can also contain formulating agents, such as suspending, stabilizing and/or dispersing agent. The composition for injection can be presented in unit dosage form, e.g., in ampules or in multidose containers, and can contain added preservatives.

Alternatively, the injectable composition can be provided in powder form for reconstitution with a suitable vehicle, including but not limited to sterile pyrogen free water, buffer, dextrose solution, etc., before use. To this end, non-human animal ApoA-I protein can be lyophilized, or the co-lyophilized protein-lipid complex can be prepared. The stored compositions can be supplied in unit dosage forms and reconstituted prior to use in vivo.

For prolonged delivery, the non-human animal ApoA-I protein can be formulated as a depot composition, for administration by implantation; e.g., subcutaneous, intradermal, or intramuscular injection. Thus, for example, the non-human animal ApoA-I protein can be formulated with suitable polymeric or hydrophobic materials (e.g., as an emulsion in an acceptable oil) or ion exchange resins, or as sparingly soluble derivatives; e.g., as a sparingly soluble salt form of non-human animal ApoA-I protein.

Alternatively, transdermal delivery systems manufactured as an adhesive disc or patch which slowly releases the active ingredient for percutaneous absorption can be used. To this end, permeation enhancers can be used to facilitate transdermal penetration of the active ingredient. A particular benefit can be achieved by incorporating non-human animal ApoA-I protein or the protein-lipid complex into a nitroglycerin patch for use in patients with ischemic heart disease and hypercholesterolemia.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Oral pharmaceutical compositions of the bovine ApoA-I protein can be conjugated with NOBEX® (Protein Delivery Inc.) polymers as described in U.S. Pat. Nos. 5,359,030; 5,438,040; 5,681,811; 6,191,105; 6,309,633 and 6,380,405, incorporated herein by reference. Liquid preparations for oral administration can take the form of, for example, solutions, syrups or suspensions, or they can be presented as a dry product for constitution with water or other suitable vehicle before use. Such liquid compositions can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The compositions can also contain buffer salts, flavoring, coloring and sweetening agents as appropriate. Compositions for oral administration can be suitably formulated to give controlled release of the active compound.

For buccal administration, the compositions can take the form of tablets or lozenges formulated in conventional manner. For rectal and vaginal routes of administration, the active ingredient can be formulated as solutions (for retention enemas) suppositories or ointments.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can, if desired, be presented in a pack or dispenser device which can contain one or more unit dosage forms containing the active ingredient. The pack can, for example, comprise metal or plastic foil, such as a blister pack. The pack or dispenser device can be accompanied by instructions for administration.

Stable non-human animal ApoA-I protein formulations that have a long shelf life can be made by lyophilizing non-human animal ApoA-I protein—either to prepare bulk for reformulation, or to prepare individual aliquots or dosage units which can be reconstituted by rehydration with sterile water or an appropriate sterile buffered solution prior to administration to a subject.

The non-human animal ApoA-I protein can be formulated and administered in a protein-lipid complex. This approach has several advantages since the complex should have an increased half-life in the circulation, particularly when the complex has a similar size and density to HDL, and especially the pre-β-1 or pre-β-2 HDL populations. The protein-lipid complexes can conveniently be prepared by any of a number of methods described below. Stable compositions having a long shelf life can be made by lyophilization—the colyophilization procedure described below being the preferred approach. See, U.S. Pat. No. 6,287,590 which is incorporated by reference herein. The non-human animal ApoA-I protein-lipid complex can be a pharmaceutical composition. See, U.S. Pat. No. 6,306,433 which is incorporated by reference herein. The lyophilized non-human animal ApoA-I protein-lipid complexes can be used to prepare bulk for pharmaceutical reformulation, or to prepare individual aliquots or dosage units which can be reconstituted by rehydration with sterile water or an appropriate buffered solution prior to administration to a subject.

A variety of methods well known to those skilled in the art can be used to prepare the protein-lipid vesicles or complexes. To this end, a number of available techniques for preparing liposome or proteoliposome compositions can be used. For example, the non-human animal ApoA-I protein can be cosonicated (using a bath or probe sonicator) with appropriate lipids to form vesicles. Alternatively the protein can be combined with preformed lipid vesicles resulting in the spontaneous formation of protein-lipid vesicles. In yet another alternative, the protein-lipid vesicles can be formed by a detergent dialysis method; e.g., a mixture of the protein, lipid and detergent is dialyzed to remove the detergent and reconstitute or form protein-lipid vesicles (See, Jonas et al., 1986, Methods in Enzymol. 128:553–582).

While the foregoing approaches are feasible, each method presents its own peculiar production problems in terms of cost, yield, reproducibility and safety. A simple method for preparing protein or protein-phospholipid complexes having characteristics similar to HDL has been developed. This method can be used to prepare non-human animal ApoA-I protein-lipid complexes, and has the following advantages: (1) Most or all of the included ingredients are used to form the designed complexes, thus avoiding waste of starting material which is common to the other methods. (2) Lyophilized compounds are formed which are very stable during storage. The resulting complexes can be reconstituted immediately before use. (3) The resulting complexes usually need not be further purified after formation and before use. (4) Toxic compounds, including detergents such as cholate, are avoided. Moreover, the production method can be easily scaled up and is suitable for GMP manufacture (e.g., in an endotoxin-free environment).

In accordance with the method, the protein and lipid are combined in a solvent system which co-solubilizes each ingredient and can be completely removed by lyophilization. To this end, solvent pairs must be carefully selected to ensure co-solubility of both the amphipathic protein and the hydrophobic lipid. In one embodiment, the non-human animal ApoA-I protein to be incorporated into the particles can be dissolved in an aqueous or organic solvent or mixture of solvents (solvent 1). The (phospho)lipid component is dissolved in an aqueous or organic solvent or mixture of solvents (solvent 2) which is miscible with solvent 1, and the two solutions are mixed. Alternatively, the protein and lipid can be incorporated into a co-solvent system; i.e., a mixture of the miscible solvents. A suitable proportion of protein (protein) to lipids is first determined empirically so that the resulting complexes possess the appropriate physical and chemical properties; i.e., usually (but not necessarily) similar in size to HDL. The resulting mixture is frozen and lyophilized to dryness. Sometimes an additional solvent must be added to the mixture to facilitate lyophilization. This lyophilized composition can be stored for long periods and will remain stable.

For example non-human animal ApoA-I protein and phospholipids can be dissolved separately in methanol, combined, then mixed with xylene before lyophilization. The protein and lipid can both be added to a mixture of the two solvents. Alternatively, a solution of the protein dissolved in methanol can be mixed with a solution of lipid dissolved in xylene. Care should be taken to eliminate salt from the solvent system in order to avoid salting out the protein. The resulting solution containing the protein and lipid cosolubilized in methanol/xylene is lyophilized to form a powder.

The lyophilized composition can be reconstituted in order to obtain a solution or suspension of the protein-lipid complex. To this end, the lyophilized powder is rehydrated with an aqueous solution to a suitable volume (often 5 milligrams protein per milliliter which is convenient for intravenous injection). In certain embodiments the lyophilized powder is rehydrated with phosphate buffered saline or a physiological saline solution. The mixture can be agitated or vortexed to facilitate rehydration, and in most cases, the reconstitution step should be conducted at a temperature equal to or greater than the phase transition temperature of the lipid component of the complexes. Within minutes, a clear solution of reconstituted lipid-protein complexes results.

An aliquot of the resulting reconstituted composition can be characterized to confirm that the complexes in the preparation have the desired size distribution; e.g., the size distribution of HDL. Gel filtration chromatography can be used to this end. For example, Pharmacia Superose 6 FPLC gel filtration chromatography system can be used. The buffer used contains 150 mM NaCl in 50 mM phosphate buffer, pH 7.4. A typical sample volume is 20 to 200 microliters of complexes containing 5 milligrams protein per milliliter. The column flow rate is 0.5 milliliters/min. A series of proteins of known molecular weight and Stokes' diameter as well as human HDL are used as standards to calibrate the column. The proteins and lipoprotein complexes are monitored by absorbance or scattering of light of wavelength 254 or 280 nm.

The non-human animal ApoA-I protein can be complexed with a variety of lipids, including saturated, unsaturated, natural and synthetic lipids and/or phospholipids. Suitable lipids include, but are not limited to, small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, sphingomyelin, sphingolipids, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, dipalmitoylsphingomyelin, distearoylsphingomyelin, phosphatidic acid, galactocerebroside, gangliosides, cerebrosides, dilaurylphosphatidylcholine, (1,3)-D-mannosyl-(1,3) diglyceride, aminophenylglycoside, 3-cholesteryl-6'-(glycosylthio)hexyl ether glycolipids, and cholesterol and its derivatives.

Accordingly, in certain preferred embodiment, non-human animal ApoA-I protein is administered as a complex with sphingomyelin. The non-human animal ApoA-I protein-lipid complex can be a pharmaceutical composition.

4.5 Methods of Administration

For use in the methods and compositions of the present invention, the non-human animal ApoA-I protein can be any administered by any method of administration known to those of skill in the art.

For example, the non-human animal ApoA-I protein or protein-lipid complexes can be administered by any suitable route that ensures bioavailability in the circulation. This can best be achieved by parenteral routes of administration, including intravenous (IV), intramuscular (IM), intradermal, subcutaneous (SC) and intraperitoneal (IP) injections. However, other routes of administration can be used. For example, absorption through the gastrointestinal tract can be accomplished by oral routes of administration (including but not limited to ingestion, buccal and sublingual routes) provided appropriate compositions (e.g., enteric coatings) are used to avoid or minimize degradation of the active ingredient, e.g., in the harsh environments of the oral mucosa, stomach and/or small intestine. Alternatively, administration via mucosal tissue such as vaginal and rectal modes of administration can be utilized to avoid or minimize degradation in the gastrointestinal tract. In yet another alternative, the compositions can be administered transcutaneously (e.g., transdermally), or by inhalation. It will be appreciated that the preferred route can vary with the condition, age and compliance of the recipient.

The non-human animal ApoA-I protein or protein-lipid complex can be used therapeutically or prophylactically. That is, the non-human animal ApoA-I protein or protein-lipid complex can be administered prior to or after the presence of atherosclerotic symptoms or diagnosis of atherosclerosis. The actual dose of non-human animal ApoA-I protein or protein-lipid complex used can vary with the route of administration, pharmacokinetics and pharmacodynamics of the pharmaceutical composition, characteristics of the subject and disorder to be treated. The dose can be adjusted to achieve circulating plasma concentrations of about 5 mg/l to about 3 g/l. In certain embodiments, non-human animal ApoA-I protein can be administered by injection at a dose between about 0.5 mg/kg to about 100 mg/kg about once a week. In another embodiment, the dose is about 0.1 to about 1000 mg/kg/day. In another embodiment, the dose is about 0.1 to about 500 mg/kg/day. In another embodiment the dose is about 0.1 to about 100 mg/kg/day. In another embodiment, the dose is about 0.1 to about 5 mg/kg/day. In yet another embodiment, desirable serum levels can be maintained by continuous infusion or by intermittent infusion providing about 0.5–100 mg/kg/hr.

It will be apparent to one of skill in the art that the frequency of administration of the non-human animal ApoA-I protein or non-human animal ApoA-I protein-lipid complex can vary according to the route of administration, pharmacokinetics and pharmacodynamics of the pharmaceutical composition, characteristics of the subject and disorder to be treated. The non-human animal ApoA-I protein can be administered, for example, about once daily, about twice daily, about three times daily, about four times daily or more often. In a depot composition, for example, the non-human animal ApoA-I protein, non-human animal ApoA-I protein-lipid complex or pharmaceutical compositions thereof can be administered, for example, about once weekly, about one monthly or about once every six months.

The dosing and administration of the non-human animal ApoA-I protein or ApoA-I protein-lipid complex can be varied through the course of treatment. For example, the non-human animal ApoA-I protein or ApoA-I protein-lipid complex can be administered about once weekly for one month and then about once weekly per month thereafter. The non-human animal ApoA-I protein or ApoA-I protein-lipid complex can be administered, for example, about once weekly for one month and then about once weekly for about three months, about six months, about nine months, about twelve months, about twenty-four months, about forty-eight months or about sixty months. The non-human animal ApoA-I protein can be administered, for example, about once weekly for two months, then about monthly for six months.

In certain embodiments, the non-human animal ApoA-I protein can be given intermittently, that is administration occurring at separate intervals or the administration schedule may have periods where there is no administration of the non-human animal ApoA-I. It will be apparent to one of skill in the art, that the intervals or periods where there is no administration can vary according to patient specific factors and disease progression. For example, non-human animal ApoA-I protein can be administered about once weekly for one month and then once monthly for three months, and then not administered for about six months, wherein the administration cycle can be repeated. Such an administration schedule is provided for illustrative purposes only and should not be considered limiting.

Administration of the non-human animal ApoA-I protein or ApoA-I protein-lipid complex can continue until cardiovascular risks decrease. Such cardiovascular risks can be monitored in any manner known to one of skill in the art. Cardiovascular risk monitoring can be done, for example, by measuring HDL levels, angiography, exercise tolerance and the like.

Toxicity and therapeutic efficacy of non-human animal ApoA-I protein can be determined using standard pharmaceutical procedures in cell culture or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A non-human animal ApoA-I protein which exhibits large therapeutic indices are preferred.

4.6 Structural Analysis

The activity of the non-human animal ApoA-I protein is believed to be due to structural similarity with native human ApoA-I and ApoA-I agonists. Preferably, the non-human animal ApoA-I protein has similar secondary structure to native human ApoA-I or ApoA-I agonists, particularly the presence of amphipathic α-helices.

The helicity of the non-human animal ApoA-I protein can be conveniently determined by circular dichroism (CD), fluorescence spectroscopy and nuclear magnetic resonance (NMR), as described in U.S. Pat. Nos. 6,004,925, 6,046,166 and 6,265,377, incorporated herein by reference in its entirety.

Circular dichroism spectra of the non-human animal ApoA-I protein can be used, for example, to determine the degree of helicity of the non-human animal ApoA-I protein. In particular, far UV circular dichroism spectra, between 190 and 260 nm, can be employed in the determination of protein helicity, by determination of the mean residue ellipticity at 222 nm or by comparison to a reference spectra.

Fluorescence spectroscopy can be used to determine the secondary structural characteristics of the non-human animal ApoA-I protein. For example, fluorescence measurements can be made using labeled proteins, such as tryptophan (Trp or W) or naphtylalanine (Nal) on a Fluoromax spectrometer equipped with a Xenon lamp of 150 W and a photomultiplier recording between, for example, 290 nm and 450 nm.

Nuclear Magnetic Resonance (NMR) spectroscopic analysis of the non-human animal ApoA-I protein. One and two dimensional spectra can be obtained of the non-human animal ApoA-I proteins. For large proteins, an up-field (negative) shift for the Hα resonance in the one dimensional spectra can be a quick and convenient method of determining protein helicity.

4.7 Biological Activity

4.7.1 Dyslipidemia Activity

The dyslipidemic activity of the non-human animal ApoA-I protein can be determining by quantitation of LCAT activation activity. The LCAT activation activity assay can by any LCAT activation activity assay known to one of skill in the art. For example, the ability of non-human animal ApoA-I to activate human LCAT can be determined by using the LCAT assay, as described in U.S. Pat. Nos. 6,004,925, 6,046,166 and 6,265,377, incorporated herein by reference in its entirety. Interspecies LCAT activation activity can be determined, for example, as described by Chen et al., 1983, Biochim. Biophys. Acta 753(1): 40–6, incorporated herein by reference in its entirety.

4.7.2 Anti-Viral Activity

The non-human animal ApoA-I protein can be assayed for anti-viral activity with any anti-viral assay known to one of skill in the art. The assay can be in vivo or in vitro. See, generally, Deshpande et al., 2001, Bioorg. Med. Chem. Lett. 1: 2393–2396 and Furuta et al., 2002, Antimicrob. Agents Chemother. 46: 977–981.

The plaque reduction assay has been accepted as the 'gold standard' for determining antiviral activity of drugs against viruses such as coxsackie virus B3, influenza virus A and herpes simplex virus type 1 (HSV-1). Other procedures used for antiviral screening or testing of viral susceptibility include dye uptake assays (see Langford et al., 1995, Antiviral Res. 27: 355–365; McLaren et al., 1983, Antiviral Res. 3: 223–234; Pauwels et al., 1988, J. Virol. Methods 20: 309–321; Takeuchi et al., 1991, J. Virol. Methods 33: 61–71; Watanabe et al., 1994, J. Virol. Methods 48: 257–265.) enzyme linked immunosorbent assays (see, Leahy et al., 1994, J. Virol. Methods 48: 93–108; Myc et al., 1999, J. Virol. Methods 77: 165–177; Rabalais et al., 1987, Antimicrob. Agent Chemother. 31: 946–948) flow cytometric analysis (see, Pavic et al., 1997, Antimicrob. Agents Chemother. 41: 2686–2692; Steele-Mortimer et al., 1990, J. Virol. Methods 27: 241–252) nucleic acid hybridization (Rimmelzwaan et al., 1998, J. Virol. Methods 74: 57–66 and Standring-Cox et al., 1996, J. Virol. Methods 56: 3–11) and cytopathic effect (CPE) inhibitory assays (see Schmidtke et al., 2001, J. Virol. Methods 95: 133–143). In certain embodiments the antiviral activity of the non-human animal ApoA-I protein can be evaluated by utilization of an α-1-acid glycoprotein assay. (See, Sidwell et al., 2002, Antiviral Chem. Chemother.12:359–365.) The α-1-acid glycoprotein is an acute phase protein that is associated with conditions such as inflammation, pregnancy and cancer. The protein can be assayed by single radial immunodiffusion using a commercially available kit. (Saikin Kagaku Institute, Sendai, Japan).

4.7.3 Activity Against Septicemia

The activity of the non-human animal ApoA-I protein in bacterial infections can be achieved by any method known to those of skill in the art. The activity of the non-human animal ApoA-I protein against gram negative septicemia can be determined by any method known to those of skill in the art. The activity of the non-human animal ApoA-I protein in reducing or preventing the release of cytokines, especially TNF-α, can be achieved using, for example, the methods described by Casas et al. and Desch et al., (Casas et al., 1995, J. Surgical Res. 59:544–552, Desch et al., 1989, Lymphokine Res. 8:141–147, incorporated herein by reference in its entirety).

The in vitro method for determining TNF-α production can include the whole blood assay described by Casas et al, or Desch et al., incorporated herein by reference in its entirety. The ex vivo and in vivo methods for determining TNF-α production can be the method described by Casas et al, or Desch et al. The methods can use New Zealand White rabbits or other suitable animal models as know to those of skill in the art.

4.8 Other Uses

The invention provides methods of treating disorders in animals, including humans, associated with dyslipidemia. The invention also provides other uses of the non-human animal ApoA-I protein, non-human animal ApoA-I protein pharmaceutical compositions, non-human animal ApoA-I protein-lipid complex and pharmaceutical compositions of the non-human animal ApoA-I protein-lipid complex.

The non-human animal ApoA-I protein can be used in assays in vitro to measure serum HDL, e.g., for diagnostic purposes. Because non-human animal ApoA-I protein associates with the HDL component of serum, non-human animal ApoA-I protein can be used as "markers" for the HDL population. Moreover, non-human animal ApoA-I protein can be used as markers for the subpopulation of HDL that are effective in RCT. To this end, non-human animal ApoA-I protein can be added to or mixed with a patient serum sample; after an appropriate incubation time, the HDL component can be assayed by detecting the incorporated non-human animal ApoA-I protein. This can be accomplished using labeled non-human animal ApoA-I protein (e.g., radiolabels, fluorescent labels, enzyme labels, dyes, etc.), or by immunoassays using antibodies (or antibody fragments) specific for the ApoA-I protein.

Alternatively, labeled non-human animal ApoA-I protein can be used in imaging procedures (e.g., CAT scans, MRI scans) to visualize the circulatory system, or to monitor RCT, or to visualize accumulation of HDL at fatty streaks, atherosclerotic lesions, etc. (where the HDL should be active in cholesterol efflux).

The non-human animal ApoA-I protein can also be used as a diagnostic as described by U.S. Pat. No. 6,355,451, incorporated herein by reference. For example, labeled non-human animal ApoA-I protein, non-human animal ApoA-I protein fragment or complementary peptide or protein can be used to make a diagnostic non-human animal ApoA-I protein.

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended claims set forth below.

All references cited herein are incorporated herein by reference in their entireties for all purposes.

What is claimed is:

1. A protein-lipid complex consisting of a purified non-human animal ApoA-I protein and a lipid, wherein the lipid is sphingomyelin or dipalmitoylphosphatidylcholine, and wherein said complex activates LCAT (lecithin cholesterol acyl transferase) activity, promotes cholesterol efflux and is suitable for administration to a humans.

2. A sterile pharmaceutical composition suitable for intravenous administration into a human comprising the protein-lipid complex of claim 1 and a pharmaceutically acceptable carrier, excipient or diluent.

3. The pharmaceutical composition of claim 2 which is in the form of a solution.

4. The pharmaceutical composition of claim 2 wherein the non-human animal ApoA-I protein has greater than about 38% human lecithin-cholesterol acyltransferase (LCAT) activation activity.

5. The pharmaceutical composition of claim 2 wherein the non-human animal ApoA-I protein has greater than about 40% human LCAT activation activity.

6. The pharmaceutical composition of claim 2 wherein the non-human animal ApoA-I protein has greater than about 43% human LCAT activation activity.

7. The pharmaceutical composition of claim 2 wherein the non-human animal ApoA-I protein has greater than about 45% human LCAT activation activity.

8. The pharmaceutical composition of claim 2 wherein the non-human animal ApoA-I protein is in the amount of about 1 to about 350 mg.

9. The pharmaceutical composition of claim 8 wherein the non-human animal ApoA-I protein is in the amount of about 1 to about 35 mg.

10. The pharmaceutical composition of claim 9 wherein the non-human animal ApoA-I protein is in the amount of about 7 to about 35 mg.

11. The pharmaceutical composition of claim 2 wherein the purified non-human animal ApoA-I protein is a bovine protein.

12. The pharmaceutical composition of claim 2 wherein the purified non-human animal ApoA-I protein is a chicken protein.

13. The pharmaceutical composition of claim 2 wherein the purified non-human animal ApoA-I protein is a turkey protein.

14. The pharmaceutical composition of claim 2 wherein the purified non-human animal ApoA-I protein is a porcine protein.

15. The pharmaceutical composition of claim 2 wherein said non-human animal ApoA-I protein having greater than about 60% homology with native human ApoA-I protein.

16. The pharmaceutical composition of claim 15 wherein said non-human animal ApoA-I protein having greater than about 70% homology with native human ApoA-I protein.

17. The pharmaceutical composition of claim 16 wherein said non-human animal ApoA-I protein having greater than about 80% homology with native human ApoA-I protein.

18. The pharmaceutical composition of claim 17 wherein said non-human animal ApoA-I protein having greater than about 90% homology with native human ApoA-I protein.

19. The ApoA-I protein-lipid complex of claim 1 wherein the non-human animal ApoA-I protein is in the amount of about 1 to about 350 mg.

20. The ApoA-I protein-lipid complex of claim 19 wherein the non-human animal ApoA-I protein is in the amount of about 1 to about 35 mg.

21. The ApoA-I protein-lipid complex of claim 20 wherein the non-human animal ApoA-I protein is in the amount of about 7 to about 35 mg.

22. The ApoA-I protein-lipid complex of claim 1 wherein the non-human animal ApoA-I protein has greater than about 38% human LCAT activation activity.

23. The ApoA-I protein-lipid complex of claim 1 wherein the non-human animal ApoA-I protein has greater than about 40% human LCAT activation activity.

24. The ApoA-I protein-lipid complex of claim 1 wherein the non-human animal ApoA-I protein has greater than about 43% human LCAT activation activity.

25. The ApoA-I protein-lipid complex of claim 1 wherein the non-human animal ApoA-I protein has greater than about 45% human LCAT activation activity.

26. The ApoA-I protein-lipid complex of claim 1 wherein said non-human animal ApoA-I protein having greater than about 60% homology with native human ApoA-I protein.

27. The ApoA-I protein-lipid complex of claim 26 wherein said non-human animal ApoA-I protein having greater than about 70% homology with native human ApoA-I protein.

28. The ApoA-I protein-lipid complex of claim 27 wherein said non-human animal ApoA-I protein having greater than about 80% homology with native human ApoA-I protein.

29. The ApoA-I protein-lipid complex of claim 28 wherein said non-human animal ApoA-I protein having greater than about 90% homology with native human ApoA-I protein.

30. The ApoA-I protein-lipid complex of claim 1 wherein said non-human animal ApoA-I protein is a bovine protein.

31. The ApoA-I protein-lipid complex of claim 1 wherein said non-human animal ApoA-I protein is a chicken protein.

32. The ApoA-I protein-lipid complex of claim 1 wherein said non-human animal ApoA-I protein is a turkey protein.

33. The ApoA-I protein-lipid complex of claim 1 wherein said non-human animal ApoA-I protein is a porcine protein.

* * * * *